US008811569B2

(12) United States Patent
Kullenberg et al.

(10) Patent No.: US 8,811,569 B2
(45) Date of Patent: Aug. 19, 2014

(54) METHOD AND APPARATUS FOR ESTIMATING THE DRY MASS FLOW RATE OF A BIOLOGICAL MATERIAL

(71) Applicant: Mantex AB, Kista (SE)

(72) Inventors: Ragner Kullenberg, Oskarstrom (SE); Eric Landstrom, Stockholm (SE); Fredrik Danielsson, Vasteras (SE); Christian Bergstrand, Stockholm (SE)

(73) Assignee: Mantex AB, Kista (SE)

( * ) Notice: Subject to any disclaimer, the term of this patent is extended or adjusted under 35 U.S.C. 154(b) by 65 days.

(21) Appl. No.: 13/653,164

(22) Filed: Oct. 16, 2012

(65) Prior Publication Data

US 2013/0036831 A1    Feb. 14, 2013

(30) Foreign Application Priority Data

Oct. 17, 2011 (EP) .................................... 11185475

(51) Int. Cl.
*G01N 23/06* (2006.01)
(52) U.S. Cl.
USPC ............................................................ 378/53
(58) Field of Classification Search
USPC ....................................... 378/54, 53; 250/388
See application file for complete search history.

(56) References Cited

U.S. PATENT DOCUMENTS

| 3,761,712 | A |   | 9/1973 | Listerman |
| 4,336,660 | A | * | 6/1982 | Strydom ........................ 34/389 |
| 5,452,954 | A | * | 9/1995 | Handke et al. .................. 366/16 |
| 6,493,418 | B1 |   | 12/2002 | Di |
| 8,431,276 | B2 | * | 4/2013 | Zhang et al. .................. 429/413 |
| 2011/0176658 | A1 |   | 7/2011 | Ullberg |

FOREIGN PATENT DOCUMENTS

DE    20 2007 005656    9/2008

OTHER PUBLICATIONS

Martin Kloppenburg, European Search Report, Parent EP Patent Application No. EP11185475.8, Apr. 18, 2012, The Hague, Netherlands.

* cited by examiner

*Primary Examiner* — Jewel V Thompson
(74) *Attorney, Agent, or Firm* — Babcock IP, PLLC

(57) ABSTRACT

A method and an apparatus for measuring dry mass flow rate for a biological material. The method steps include conveying the biological material through a measuring station, scanning the biological material with electromagnetic radiation of at least two different energy levels, determining the amount of radiation transmitted through the biological material at said two energy levels, and summing, for each of sad two energy levels, the radiation transmission values over a time frame to summed radiation transmission values. Further, a wet dry mass flow rate is estimated based on the summed radiation transmission values for said two energy level. The moisture content of the biological material is estimated based on the amounts of radiation transmitted through the biological material. The estimated wet dry mass flow rate is scaled in accordance with the estimated moisture content of the biological material, thereby providing an estimate of the dry mass flow rate.

18 Claims, 1 Drawing Sheet

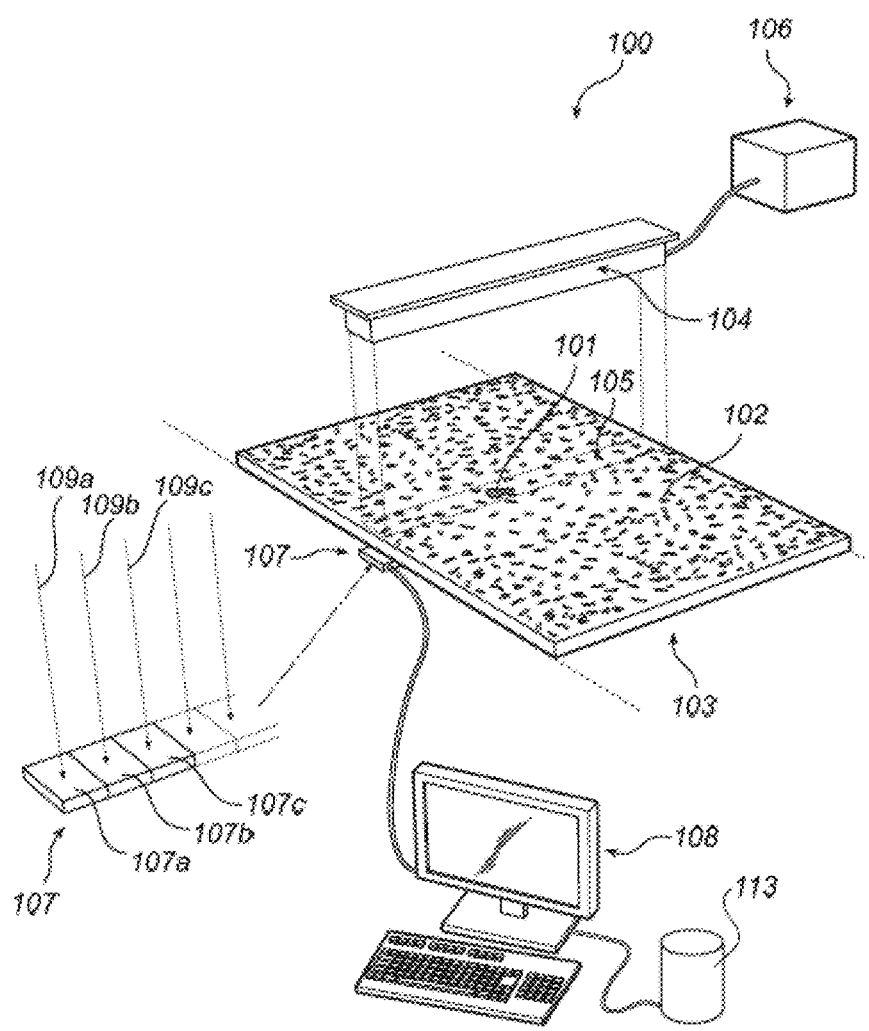

METHOD AND APPARATUS FOR ESTIMATING THE DRY MASS FLOW RATE OF A BIOLOGICAL MATERIAL

TECHNICAL FIELD OF THE INVENTION

The present invention relates to a method and an apparatus for measuring the dry mass flow rate of a biological material in an automated procedure. The invention is particularly useful for measuring the moisture content in wood, such as wood chips.

BACKGROUND

In the wood industry it is of great importance to obtain precise measurements of the mass flow rate, and in particular the dry mass flow rate, in the material to be processed, in order to achieve improved control of the process parameters. A precise knowledge of the dry mass flow rate in the material is of a central importance for the quality of the end product in many processes within the wood and pulp industry. For example, the optimal amount of chemicals to be added in the processes is dependent on the dry mass flow rate, and in order to control the processes adequately it is of great importance to correctly estimate the dry mass flow rate in the material.

Previously known methods to estimate the dry mass flow rate is based on cumbersome and tedious measurements made on samples of the biological material, and subsequent estimations based on an estimated mass flow rate etc. However, it would normally take a day or more until a correct measure value could be obtained, which delays the overall processing. It is therefore a need for a fast and reliable method to estimate the dry mass flow rate.

Similar needs exist in other industries handling biological material. For example, it would be advantageous to have a fast and reliable method for estimating the dry mass flow rate in the biological material in the bio energy field, in order to control the burning process more precisely, and improve its efficiency.

An automated procedure for estimating a wet mass flow is disclosed in U.S. Pat. No. 6,493,418. However, apart from being directed to determining a wet mass flow, which is less useable for the industry, the proposed method is relatively simple, and would seemingly provide a relatively low accuracy and reliability.

There is therefore a need for a fast and accurate method and apparatus for estimating the dry mass flow rate of a biological material, such as in wood, which can e.g. be used directly by people in field work operation, be used in automated processes, and the like.

SUMMARY OF THE INVENTION

It is therefore an object of the present invention to provide an improved method and apparatus for measuring the dry mass flow rate in a biological material in an automated process, which overcome or at least alleviate the above-discussed problems of the prior art.

This object is achieved by means of the invention as defined in the appended claims.

According to a first aspect of the invention there is provided a method for estimation of dry mass flow rate in a biological material in an automated procedure, comprising the steps of:

conveying the biological material through a measuring station;

scan the biological material conveyed through the measuring station with electromagnetic radiation of at least two different energy levels;

determine the amount of radiation transmitted through said biological material at said two energy levels;

summing, for each of sad two energy levels, the radiation transmission values over a time frame to summed radiation transmission values;

estimate a wet dry mass flow rate, M_wet, based on the summed radiation transmission values for said two energy levels;

estimate the moisture content, MoistC, of said biological material based on said determined amounts of radiation transmitted through the biological material; and scaling the estimated wet dry mass flow rate, M_wet, in accordance with said estimated moisture content, MoistC, of the biological material, thereby providing an estimate of the dry mass flow rate, M_dry.

The term "mass flow rate" is in the context of this application used to indicate the mass of substance which passes through a given surface per unit time (kg/s). The term "wet mass flow rate" is the mass flow rate of biological material, such as chips, in its natural condition. The term "dry mass flow rate" is the mass flow rate for the biological material, such as chips, when the biological material has been dried before passing through the measuring station.

By the use of two or more energies, it becomes possible to accurately determine the moisture content of the biological material, as has previously been disclosed in application US 2011/176658 by the same applicant, said application hereby being incorporated by reference. Hereby, it becomes possible to determine the dry mass flow rate, which is far more useful for the industry than the wet mass flow rate, in an integrated and in-line procedure, enabling real-time adjustments and control of subsequent procedures.

The present invention is particularly useable for estimating the dry mass flow rate in wood chips, but it may also be used for other forms of wood, as well as for other types of biological material, such as pulp, biomass fuel, etc. The invention is particularly useful for biological material in a liquid or separated form, and preferably in the form of chips. However, the invention is also useable for other types of biological material, and in particular different types of crop, such as corn, grain and sugar canes.

By "moisture content" is in this application meant the ratio between the quantity of moisture (i.e. water) in a certain quantity of material and the total material quantity. Consequently, estimation of moisture content in a material is also, indirectly, an estimation of the non-moisture content. In e.g. wood chips, the material essentially consist of moisture and fibers, and consequently, estimation of the moisture content is also in practice an estimation of the fiber content in the material. Similarly, the moisture content may, in accordance with the present invention, be estimated either directly or indirectly by estimation of content of remaining constituents of the material.

The method of the present invention makes use of irradiation of two or more different energy levels, and determines the moisture content of the material, directly or indirectly, from the measured transmission energy, i.e. the amount of the radiation of each wavelength that is absorbed in the material. Different material types, such as different sort of wood, have different absorption coefficient. However, in many applications, only one type of biological material is used, or biological materials having similar properties. Further, if many different types of biological materials are to be used in the same process, the inventive system may compensate for this in a very effective way by using a reference database, as will be discussed further in the following.

The method/apparatus according to the present invention is very well suited for use in online measurements along conveyor lines where material is transported, on conveyor belts, in pipe-lines, etc. The present invention may be used in fully or partly automated procedures, and requires no, or very limited, operator interaction.

Even though it has been determined that two energy levels are sufficient to provide an accurate and reliable estimation of the dry mass flow, it is naturally possible to use more than two energy levels. For example, it is contemplated that three or four energy levels may be used. By increasing the number of energy levels, the accuracy and reliability may be improved even further.

The radiation scan, which preferably comprises an X-ray radiation scan, also provides X-ray images that may be used for further analysis of the biological material. Thus, the detector signals may also be used for optical analysis, e.g. for determining the type of biological material that is at hand, and other properties of the material.

The amount of radiation transmitted through the sample of the biological material at the two energy levels is preferably determined in relation to a calibration reference value. The calibration reference value can e.g. be determined by measurement of the transmission of radiation through a reference material of a predetermined thickness, which is preferably made immediately before and/or after the each measurement through the biological material, the reference material e.g. being aluminum. Hereby, it is ensured that adequate calibration is always at hand.

The scaling of the estimated wet dry mass flow rate is preferably made by multiplication of the estimated wet dry mass flow with a scaling factor being (1-MoistC).

The method further preferably comprises the step of measuring the speed of a conveying device conveying the biological material through the measuring station, and scaling the estimated wet dry mass flow rate in accordance with the deviation between said measured speed of the conveying device compared to a default speed. Hereby, the method can automatically correct for variations in speed. The measurements can be made by means of a speed gauge arranged on e.g. a conveyor belt, a rotor or wheel in the conveyor system, or the like. Preferably, the scaling is done by multiplying the estimated mass value, representing a value corresponding to a default speed $v_{def}$, with a factor $v_{meas}/v_{dev}$, where $v_{meas}$ represents the measured speed. However, for many applications, the conveying speed is a constant, and for such situations a default conveyor speed may be used without scaling.

The biological material is preferably transported on a conveyor line, wherein the biological material is irradiated with electromagnetic radiation of at least two different energy levels in a plane substantially perpendicular to a direction of advancement of said conveyor line. Further, the amount of radiation transmitted through said biological material at said two energy levels is preferably determined for a plurality of radiation paths penetrating said biological material in the plane substantially perpendicular to the direction of advancement of said conveyor line. In particular, it is preferred to use a fan shape set-up, wherein radiation paths radiate trough a plurality of paths forming a fan shaped appearance. Hereby, a large amount, or even all, of the biological material being conveyed through the measuring station is irradiated and measured.

The radiation transmission values are preferably provided in the form of R estimates, R being $R_x=\ln(N_{0x}/N_x)$, i.e the natural logarithm of the quotient between a calibrated reference value for the transmission $N_{0x}$ and the transmission value through the biological material N, at an energy level x, wherein the estimation of the wet dry mass flow rate comprises a sum of linear components of $RS_x$, where $RS_x$ are the summed $R_x$ values over a time frame. The use of such R and RS values has proven very effective. The time frames for estimation of the RS values are preferably a fixed, predetermined time value, but varying time frames may also be used. Further, the time frames may be consecutive or overlapping. A suitable time frame for estimation of RS values is in the range of 0.1-5.0 seconds, and preferably in the range 0.5-2.0 seconds, and most preferably around 1 second. The dry mass flow values are preferably presented as a mean value for a certain time period, such as for a time period in the range 10-120 seconds, and preferably a time period in the range 15-60 seconds, and most preferably about 30 seconds.

The linear components of the $RS_x$ are typically summed as $aRS_1+bRS_2$, if two energy levels are used, wherein a and b are coefficients determinable by calibration measurements.

Preferably, the estimation of the wet dry mass flow further comprises a mixed component, in which the $RS_x$ values for said at least two energy levels are either multiplied or divided. In a preferred embodiment, the estimation of the wet dry mass flow is made according to the formula: $M\_wet=a+bRS_1RS_2+cRS_1+dRS_2$, where a-d are coefficient determinable through calibration measurements. Alternatively, the estimation of the wet dry mass flow can be made according to the formula: $M\_wet=a+bRS_1/RS_2+cRS_1+dRS_2$, where again a-d are coefficients determinable through calibration measurements.

For calibration, a known quantity of biological material, with known or subsequently determined mass, may be measured.

The estimation of the moisture content preferably comprises the steps of:

providing a reference database for a plurality of different material types with known moisture content;

identify a material type in said reference database most resembling the biological material of the biological material of the sample; and determine the moisture content of said sample of biological material based on said identified material type and said determined amounts of radiation transmitted through the sample.

Hereby, the use of different types of biological materials in the same process can easily be handled directly, an in an automated fashion. The data for the reference database is preferably assembled by measuring transmission of electromagnetic radiation of at least two different energy levels through a plurality of different material types, and by measuring the moisture content of said materials by means of a conventional method, and preferably by controlled drying. The material types may e.g. be different sorts of wood, such as birch, spruce, pine, oak, and alder. Hereby, the same type of measurement data as obtained with the subsequent measurement of new materials can be related to exactly measured moisture content data. Since the reference database needs only be created during the initialization and can then be reused repeatedly, there is no particular need for speedy processes during these reference database measurements.

The scanning of a sample of the biological material with electromagnetic radiation of at least two different energy levels preferably comprises arranging the biological material in a separated form, and preferably in the form of chips.

The amount of radiation transmitted through the sample of the biological material at said two energy levels is preferably determined in relation to a calibration reference value. The calibration reference value can e.g. determined by measurement of the transmission of radiation through a reference material of a predetermined thickness, said calibration measurement preferably being made immediately before and/or after the each measurement through the biological material, the reference material preferably being aluminum.

The scanning of the sample of the biological material with electromagnetic radiation of at least two different energy levels preferably comprises a first scan with a first energy level, and a subsequent second scan with a second energy level. Hereby, the devices for scanning the biological material may be arranged in sequence after each other, so that the biological material is first conveyed through a first scanning zone, and immediately thereafter conveyed through a second scanning zone. However, it is also feasible to perform the measurements with the two energy levels simultaneously, in one single scanning zone.

The at least two different energy levels are both preferably of X-ray radiation wavelengths. Further, the radiation of both said energy levels are preferably emitted from a single radiation source operating in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

According to another aspect of the present invention, there is provided an apparatus for measuring dry mass flow rate in a biological material in an automated procedure, comprising:
  a measuring station; and
  a conveyor device arranged to conveying the biological material through a measuring station;
wherein the measuring station comprises:
  a scanning device for scanning the biological material with electromagnetic radiation of at least two different energy levels;
  a detector for determining the amount of radiation transmitted through said biological material at said two energy levels; and
  a processor for determining, for each of sad two energy levels, a sum of the radiation transmission values over a time frame to summed radiation transmission values, for estimating a wet dry mass flow rate, M_wet, based on the summed radiation transmission values for said two energy levels, for estimating the moisture content, MoistC, of said biological material based on said determined amounts of radiation transmitted through the biological material; and for scaling the estimated wet dry mass flow rate, M_wet, in accordance with said estimated moisture content, MoistC, of the biological material, thereby providing an estimate of the dry mass flow rate, M_dry.

Similar advantages and preferred embodiments as discussed above in relation to the first aspect of the invention are related to this second aspect of the invention.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIG. 1 schematically illustrates a measurement device for estimating a dry mass flow rate in a biological material transported on a conveyor line.

DETAILED DESCRIPTION OF PREFERRED EMBODIMENTS

FIG. 1 schematically illustrates an embodiment of a measurement device 100 for estimating a dry mass flow rate of a biological material 102 transported on a conveyor line 103. The biological material 102 may typically be wood chips, or other biomass fuels.

If the height and properties of the material varies, it is preferred to scan essentially all of the material moved past the measurement device. If there is no significant variation in height and material properties over time, it may suffice to measure in a single point or target area.

In order to scan essentially all of the material, the measurement device comprises a radiation source 104 adapted to irradiate a target area 105 that spans across the width of the conveyor line. The radiation source 104 is adapted to provide radiation of at least two different energy levels/wavelengths. Preferably, the radiation source is an X-ray tube for provision of X-ray radiation of two or more different wavelengths. Preferably, the X-ray tube operates in the range 20-150 kVp. The output radiation from the radiation source is preferably directed towards the target area through a collimator and a lens (not shown). The radiation source 104 is controlled by means of a controller 106.

Alternatively, the radiation source 104 may comprise two or several separate juxtaposed radiation tubes, wherein the juxtaposed radiation sources radiate the different wavelengths either simultaneously or sequentially. However, preferably the different wavelength radiation traverses the material to be measured along essentially the same path. When radiation of two (or more) wavelengths is emitted simultaneously from the radiation source the intensity of the two signals should preferably be measured individually. This may be effected directly by making provisions such that certain portions of the detector by filtration only measure radiation having a certain energy level while others measure other energy levels. It may also be effected by subsequent treatment of signals, allowing superimposed signals to be separated.

On the opposite side of the target area 105, a detector 107 is arranged to receive radiation transmitted through material located in the target area 105. The detector is preferably a semiconductor detector comprising a linear array of semiconductor detector areas 107a-c distributed across the width of the conveyor line. The detector 107 is connected to a control unit 108 with a processor, e.g. an ordinary personal computer. The control unit receives detection data from the detector through a suitable interface, such as through a USB port.

In operation, the radiation source 104 irradiates the material in the target area 105 with electromagnetic radiation of at least two different energy levels. This may be achieved by sequentially irradiating the material with radiation of a first wavelength, and radiation of a second wavelength, i.e. the radiation source initially emits rays having one wavelength and then, by altering the voltage across the radiation tube, a different wavelength.

For each energy level, the amount of radiation transmitted through the material located in the target area 105 is measured on the opposite side of the target area 105 by the detector areas 107a-c of the detector, wherein each detector area 107a-c receives radiation that has penetrated the material 102 along a different radiation path 109a-c.

In order to get a reference value for calibration, it is preferred to measure a calibration material. This can be achieved, for example, by measuring without any biological material present. Thus, in this case, a calibration measurement is obtained with air as a calibration material. Alternatively, the biological material may be replaced with a calibration material with known properties, such as aluminum. The calibration measurements may be obtained before measuring of the biological material, during initialization, or repeatedly during the process. Alternatively, calibration measurements may be obtained by relocating the radiation source 104 and the detector 107 to a location next to the conveyor line such that the radiation passes through air only on its way from the radiation source to the detector. It is also possible to use additional radiation sources and detectors situated on one or both sides of the conveyor belt.

Based on these calibration measurements, calibration values are determined as:

$$N_{01,02} = N_{Air1,2} \exp(\mu x)$$

where $N_{01}$ and $N_{02}$ are the calibration values for energy level 1 and 2, respectively, $N_{Air1}$ and $N_{Air2}$ are the detected transmission values after passage through the known distance of air or known material, $\mu$ is the known attenuation coefficient for air or known material ($cm^{-1}$) and x is the known distance of air or known material (cm) that separates the radiation source and the detector.

Based on the measured radiation transmission values for the at least two energy level used, the moisture content of the biological material is determined.

To this end, a reference database may be provided, connected to the control unit 6, with data concerning at least detected transmission values for the radiation at the different energy levels, and moisture content values, for different types of biological material, such as for a number of different sorts of wood.

However, as discussed previously, if the type of biological material is known beforehand, the estimation of the moisture content, MoistC, may be simplified.

Further, for estimation of a wet mass flow rate, the radiation transmission values for the two energy level are summed over a time frame to summed radiation transmission values, and from these summed radiation transmission values, an estimate of the wet dry mass flow rate, M_wet is provided.

The radiation transmission values are preferably provided in the form of R estimates, R being $R_x = \ln(N_{0x}/N_x)$, i.e the natural logarithm of the quotient between a calibrated reference value for the transmission $N_{0x}$ and the transmission value through the biological material $N_x$ at an energy level x, wherein the estimation of the wet dry mass flow rate comprises a sum of linear components of $RS_x$, where $RS_x$ are the summed $R_x$ values over a time frame. The use of such R and RS values has proven very effective. The time frames for estimation of the RS values are preferably a fixed, predetermined time value, but varying time frames may also be used. Further, the time frames may be consecutive or overlapping. A suitable time frame for estimation of RS values is 1 second and the dry mass flow values may be updated as a mean over the last 30 seconds.

The linear components of the $RS_x$ may be summed as $aRS_1 + bRS_2$, it two energy levels are used, wherein a and b are coefficients determinable by calibration measurements.

Preferably, the estimation of the wet dry mass flow further comprises a mixed component, in which the $RS_x$ values for said at least two energy levels are either multiplied or divided. In a preferred embodiment, the estimation of the wet dry mass flow is made according to the formula: $M\_wet = a + bRS_1RS_2 + cRS_1 + dRS_2$, where a-d are coefficient determinable through calibration measurements. Alternatively, the estimation of the wet dry mass flow can be made according to the formula: $M\_wet = a + bRS_1/RS_2 + cRS_1 + dRS_2$, where again a-d are coefficients determinable through calibration measurements.

For calibration, a known quantity of biological material, with known or subsequently determined mass, may be measured.

Based on the estimated wet mass flow rate, M_wet, and the estimated moisture content, MoistC, it is now possible to determine the dry mass flow rate, M_dry. This can e.g. be done by scaling the estimated wet mass flow rate in accordance with the determined moist value, by multiplying M_wet with a scaling factor being (1-MoistC).

If the speed of the conveyor line is varying, a scaling related to the actual conveyor speed may also be performed. In such a case, the method further preferably comprises the step of measuring the speed of the conveying device conveying the biological material through the measuring station, and scaling the estimated wet dry mass flow rate in accordance with the deviation between said measured speed of the conveying device compared to a default speed. The measurements can be made by means of a speed gauge arranged on e.g. a conveyor belt, a rotor or wheel in the conveyor system, or the like. Preferably, the scaling is done by multiplying the estimated mass value, representing a value corresponding to a default speed $v_{def}$, with a factor $v_{meas}/v_{def}$, where $v_{meas}$ represents the measured speed. However, for many applications, the conveying speed is a constant, and for such situations a default conveyor speed may be used without scaling.

In experimental testing it has been established that a "plane" model, estimating the wet mass flow rate according to a formula $M\_wet = a + bRS_1 + cRS_2$ provides a good estimate of the wet mass flow rate in most situations. However, the more complex formula, estimating the wet mass flow rate according to the formula: $M\_wet = a + bRS_1/RS_2 + cRS_1 + dRS_2$ provides increased robustness, e.g. when there is contaminations in the biological material. Further, an estimation according to a "torsion" model, estimating the wet mass flow rate according to the the formula $M\_wet = a + bRS_1RS_2 + cRS_1 + dRS_2$, has proven equally robust, and also provides improved metrics and increased robustness when the belt is empty or nearly empty.

Specific embodiments of the invention have now been described. However, several alternatives are possible, as would be apparent for someone skilled in the art. For example, the radiation need not be X-ray, but other types of electromagnetic radiation may also be used. Further, there are various ways of determining the type of biological material, both automatically and semi-automatically. Depending on the intended line of use, the reference database can be customized to comprise only the most probable material types, or comprise a large variety of different material types. Still further, the implementation of the control and processing method could be accomplished in different ways, such as in especially dedicated hardware or in software for control of already existing control means.

Further, the radiation paths through the material may be arranged in various ways. For example, the paths may travel essentially along a single line, between a radiation source and a detector, or several detectors arranged overlapping or close to each other. However, the radiation paths may also be arranged along parallel lines, to form a "curtain" like measurement zone. It is also possible to use a plurality of non-parallel paths, e.g. extending from a single radiation source to a plurality of spread out detectors, to form a "fan shaped" measurement zone. Similarly, it would also be possible to use a plurality of separated radiation emerging points, and a single detection point, or the like. Many other types of geometries for the paths are also feasible.

Such and other obvious modifications must be considered to be within the scope of the present invention, as it is defined by the appended claims. It should be noted that the abovementioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

We claim:

1. A method for estimation of dry mass flow rate in a biological material in an automated procedure, comprising the steps of:
    conveying the biological material through a measuring station;
    scan the biological material conveyed through the measuring station with electromagnetic radiation of at least two different energy levels;
    determine the amount of radiation transmitted through said biological material at said two energy levels;
    summing, for each of sad two energy levels, the radiation transmission values over a time frame to summed radiation transmission values;
    estimate a wet dry mass flow rate, M_wet, based on the summed radiation transmission values for said two energy levels;
    estimate the moisture content, MoistC, of said biological material based on said determined amounts of radiation transmitted through the biological material; and
    scaling the estimated wet dry mass flow rate, M_wet, in accordance with said estimated moisture content, MoistC, of the biological material, thereby providing an estimate of the dry mass flow rate, M_dry.

2. The method of claim 1, wherein the scaling of the estimated wet dry mass flow rate is made by multiplication of the estimated wet dry mass flow with a scaling factor being (1-MoistC).

3. The method of claim 1, further comprising the step of measuring the speed of a conveying device conveying the biological material through the measuring station, and scaling the estimated wet dry mass flow rate in accordance with the deviation between said measured speed of the conveying device compared to a default speed.

4. The method of claim 1, wherein the radiation transmission values are provided in the form of R estimates, R being $R_x = \ln(N_{0x}/N_x)$, i.e the natural logarithm of the quotient between a calibrated reference value for the transmission $N_{0x}$ and the transmission value through the biological material $N_x$ at an energy level x, wherein the estimation of the wet dry mass flow rate comprises a sum of linear components of $RS_x$, where $RS_x$ are the summed $R_x$ values over a time frame.

5. The method of claim 4, wherein the estimation of the wet dry mass flow further comprises a mixed component, in which the $RS_x$ values for said at least two energy levels are either multiplied or divided.

6. The method of claim 5, wherein the estimation of the wet dry mass flow is made according to the formula: $M\_wet = a + bRS_1RS_2 + cRS_1 + dRS_2$, where a-d are coefficient determinable through calibration measurements.

7. The method of claim 5, wherein the estimation of the wet dry mass flow is made according to the formula: $M\_wet = a + bRS_1/RS_2 + cRS_1 + dRS_2$, where a-d are coefficients determinable through calibration measurements.

8. The method of claim 1, wherein the estimation of the moisture content comprises the steps of:
    providing a reference database for a plurality of different material types with known moisture content;
    identify a material type in said reference database most resembling the biological material of the biological material of the sample; and
    determine the moisture content of said sample of biological material based on said identified material type and said determined amounts of radiation transmitted through the sample.

9. The method of claim 1, wherein the scanning of a sample of the biological material with electromagnetic radiation of at least two different energy levels comprises arranging the biological material in a separated form.

10. The method of claim 1, wherein the amount of radiation transmitted through the sample of the biological material at said two energy levels is determined in relation to a calibration reference value.

11. The method of claim 10, wherein the calibration reference value is determined by measurement of the transmission of radiation through a reference material of a predetermined thickness.

12. The method of claim 1, wherein the scanning of the sample of the biological material with electromagnetic radiation of at least two different energy levels comprises a first scan with a first energy level, and a subsequent second scan with a second energy level.

13. The method of claim 1, wherein the at least two different energy levels both are of X-ray radiation wavelengths.

14. The method of claim 1, wherein the radiation of both said energy levels are emitted from a single radiation source operating in the energy range 20-150 kVp.

15. An apparatus for measuring dry mass flow rate in a biological material in an automated procedure, comprising:
    a measuring station; and
    a conveyor device arranged to conveying the biological material through a measuring station;
    wherein the measuring station comprises:
        a scanning device for scanning the biological material with electromagnetic radiation of at least two different energy levels;
        a detector for determining the amount of radiation transmitted through said biological material at said two energy levels; and
        a processor for determining, for each of sad two energy levels, a sum of the radiation transmission values over a time frame to summed radiation transmission values, for estimating a wet dry mass flow rate, M_wet, based on the summed radiation transmission values for said two energy levels, for estimating the moisture content, MoistC, of said biological material based on said determined amounts of radiation transmitted through the biological material; and for scaling the estimated wet dry mass flow rate, M_wet, in accordance with said estimated moisture content, MoistC, of the biological material, thereby providing an estimate of the dry mass flow rate, M_dry.

16. The method of claim 9, wherein the biological material in a separated form is in the form of chips.

17. The method of claim 11, wherein the calibration measurement is made immediately before and/or after each measurement through the biological material.

18. The method of claim 11, wherein the reference material is aluminum.

* * * * *